United States Patent

Ishimitsu

[11] Patent Number: 5,881,162
[45] Date of Patent: *Mar. 9, 1999

[54] IMAGE READING APPARATUS CAPABLE OF ELIMINATING MOIRE ON IMAGES

[75] Inventor: Yoshiyuki Ishimitsu, Tokyo, Japan

[73] Assignee: Konica Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 528,952

[22] Filed: Sep. 15, 1995

[30] Foreign Application Priority Data

Sep. 20, 1994 [JP] Japan .................................. 6-225082

[51] Int. Cl.$^6$ .................................................. G06K 9/00
[52] U.S. Cl. ...................... 382/132; 250/370.9; 250/587; 378/165; 382/261; 382/264; 382/306
[58] Field of Search .................................... 382/128, 132, 382/264, 261, 306; 250/370.09, 369, 587, 559.01–559.06; 378/62, 98, 146, 164, 166

[56] References Cited

U.S. PATENT DOCUMENTS

| | | | |
|---|---|---|---|
| 4,282,546 | 8/1981 | Reitmeier | 348/580 |
| 4,918,715 | 4/1990 | Krupnick et al. | 378/164 |
| 5,006,708 | 4/1991 | Itoh et al. | 250/587 |
| 5,028,784 | 7/1991 | Arakawa et al. | 250/327.2 |
| 5,131,059 | 7/1992 | Kobayashi et al. | 382/270 |
| 5,272,547 | 12/1993 | Suzuki | 358/479 |
| 5,381,457 | 1/1995 | Burns | 378/166 |
| 5,489,782 | 2/1996 | Wernikoff | 250/369 |
| 5,548,540 | 8/1996 | Staver et al. | 364/724.1 |
| 5,565,930 | 10/1996 | Bolger et al. | 348/572 |
| 5,570,088 | 10/1996 | Rhodes | 348/441 |

FOREIGN PATENT DOCUMENTS 198265  8/1990  Japan .............................. H04N 1/04

OTHER PUBLICATIONS

Ollinger, Reconstruction–Reprojection Processing of Transmission Scans and the Variance of PET Images, 1991, pp. 1696–1699.

McKay et al., Implementation of a Multi–Channel Biomagnetic Measurement System Using DSP Technology, 1993, pp. 1090–1093.

"Analysis of the Digital Filter of which the Word Length is Limited, and the Optimum Designing Method", 1977, pp. 100–113, Nikkei Electronics, Japan, with partial English translation.

TANIGAWA et al, "Vertical Direction Resolution Characteristics for Frame–Transfer CCD Imager", vol. J59–C, No. 7 p. 451, Electronic Communication Society, Japan, with partial English translation.

*Primary Examiner*—Joseph Mancuso
*Assistant Examiner*—Timothy M. Johnson
*Attorney, Agent, or Firm*—Frishauf, Holtz, Goodman, Langer & Chick

[57] ABSTRACT

An image reading apparatus which includes a primary scanner for scanning an original X-ray image obtained using a grid and recorded on a recording medium with light in a primary scanning direction. A clock signal generator generates clock signals having a frequency N times as high as a frequency of pixel clock signals, wherein the pixel clock signals correspond to a desired pixel size, and wherein N is a positive integer. A converter converts a light beam from the recording medium into electric signals by a scanning operation of the primary scanner, and converts the electric signals into digital signals based on the clock signals. A low pass filter is provided which has at least one set of filter characteristics having a cut-off frequency between $\frac{1}{3}$ and $\frac{2}{3}$ of the frequency of the pixel clock signals for filtering the digital signals converted by the converter. A thinning mechanism thins out the filtered digital signals to 1/N in the primary scanning direction, and a memory stores a plurality of the filtering characteristics of the low pass filter. The plurality of the filtering characteristics includes the cut-off frequency of $\frac{1}{3}$ of the frequency of the pixel clock signals, and the low pass filter has a filtering characteristic which is selected in relation to a grid density of the grid and at least one of the desired pixel size and the frequency of the pixel clock signals.

8 Claims, 8 Drawing Sheets t1 : TIME t1 BEGINS AT THE COMPUTATION START
     POINT (CC0) IMMEDIATELY AFTER H-Sync.
t2 : RESET TIME
t3 : DATA SUBJECTED TO FILTERING FOR THE FIRST
     TIME AFTER H-Sync IS OUTPUTTED.
     (OUTPUT DATA AT THIS TIME CORRESPONDS TO
     THE DATA SUBJECTED TO A/D CONVERSION AT
     THE POINT OF TIME t2.)

FIG. 8
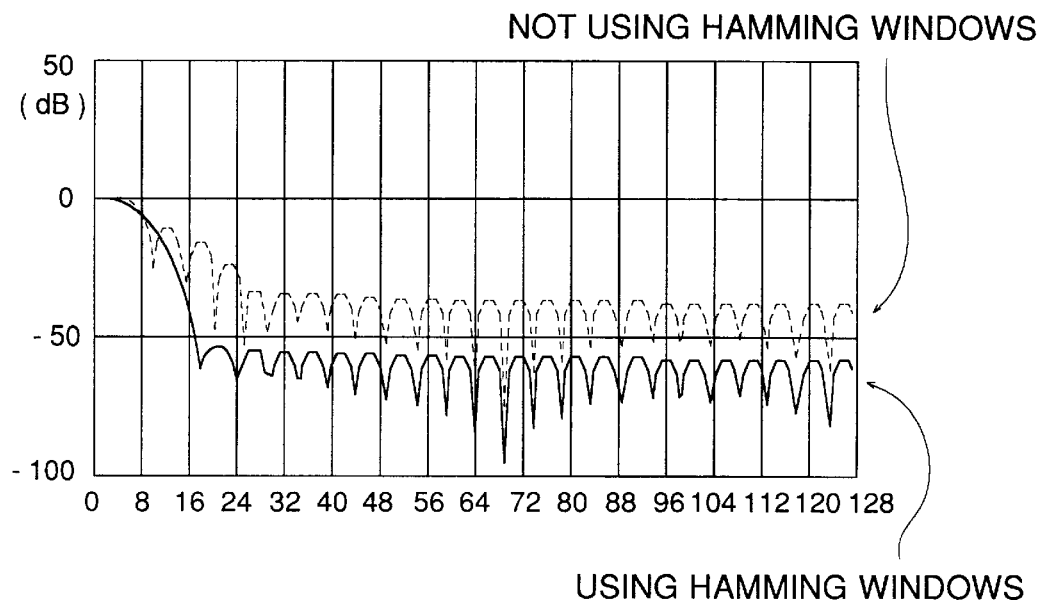
NOT USING HAMMING WINDOWS
USING HAMMING WINDOWS
FIG. 9 (a)
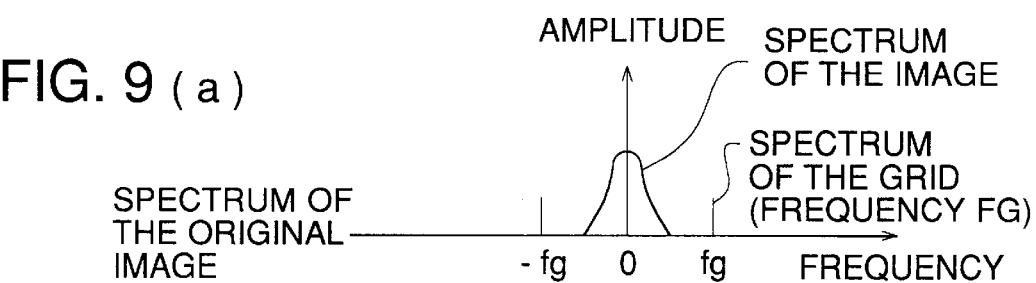
SPECTRUM OF THE ORIGINAL IMAGE
AMPLITUDE
SPECTRUM OF THE IMAGE
SPECTRUM OF THE GRID (FREQUENCY FG)
FIG. 9 (b) $fg < \frac{Fs}{2}$
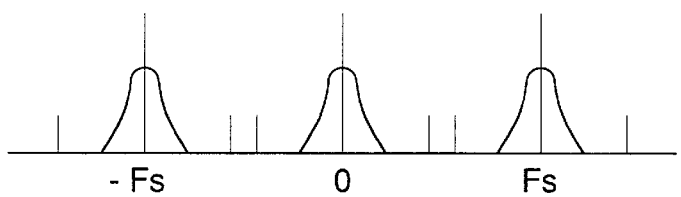
FIG. 9 (c) $fg > \frac{Fs}{2}$
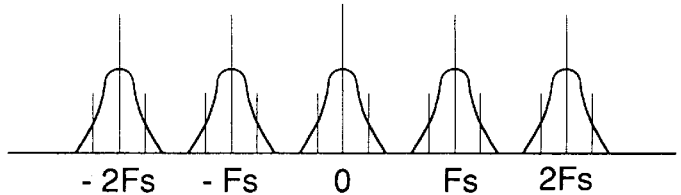

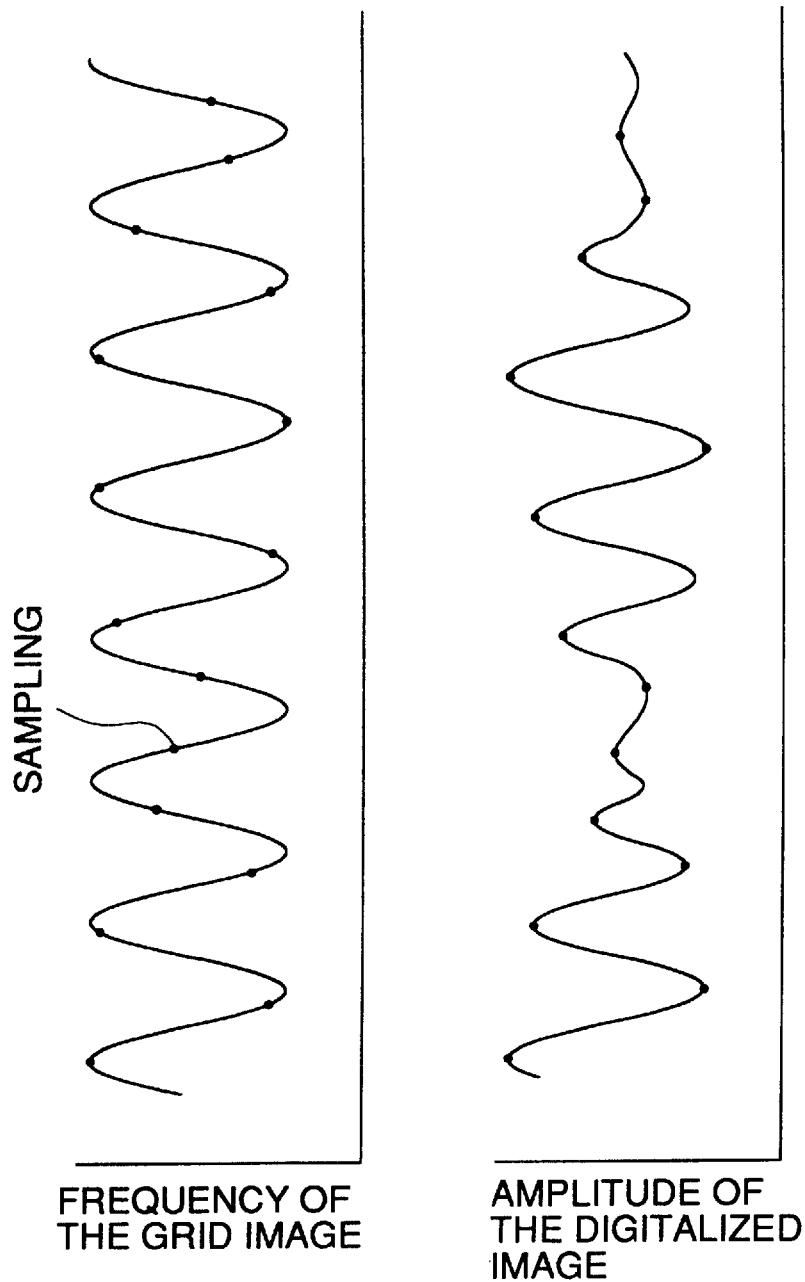

IMAGE READING APPARATUS CAPABLE OF ELIMINATING MOIRE ON IMAGES

BACKGROUND OF THE INVENTION

The present invention relates to an image reading apparatus used for reading images for medical use in which: an X-ray image for medical use recorded on a recording medium is subjected to 2-dimensional optical scanning using a light beam; transmitted light and stimulatively emitted light is converted into an electric signal; and the thus obtained electric signal is subjected to analog-digital conversion and sent out to a computer as image data.

In the case of taking an X-ray image for medical use, in order to remove X-rays diffused in the body of a patient, a filter referred to as a grid is frequently used. Therefore, an image of the grid is photographed on the X-ray image when the grid is used. The grid image is composed of longitudinal stripes disposed at regular intervals. Examples of the density of the stripes are: 34, 40, and 80 pieces/cm. That is, the intervals of the longitudinal stripes are various. When an image formed on a recording medium on which the grid is photographed is subjected to optical scanning so as to digitalize the image data, the following phenomenon appears. According to a relation between a sampling spatial frequency ($F_s$) corresponding to the frequency of analog-digital conversion and a grid spatial frequency ($F_g$) appearing when the grid image is optically scanned, aliasing is caused in the frequency region, so that a low frequency component, which is not on the original image, appears on the digital image. This is referred to as moire artifacts caused by aliasing. When a digitalized medical image is outputted onto CRT or film so as to make medical diagnosis, these moire strips are obstacles to success of medical diagnosis. FIGS. 9(a) to 9(d) are views showing a mechanism of generation of moire artifacts. In order to prevent the generation of moire patterns, $F_s$ and $F_g$ must satisfy the following inequality.

$$F_s > 2 \cdot F_g \quad (1)$$

The above is a well-known fact referred to as Nyquist's Sampling Theory. In order to realize this, for example, the following technique is disclosed in Japanese Patent Publication No. 198265/1990. For the purpose of satisfying the Nyquist Sampling Theory, an electric analog filter is applied to the image reading apparatus so that the maximum spatial frequency component ($F_{max}$) in the image signal can satisfy the following equation.

$$F_{max} = F_s/2 \quad (2)$$

As a result, after the amplitude of the grid image signal has been reduced, the A/D-conversion is carried out.

Recently, an image reading apparatus has been developed in which the pixel size can be variously changed in the process of digitalization. In this type of apparatus, $F_s$ can be made variable. In accordance with the above expression (2), it is necessary that the cut-off characteristic of the analog filter is made to be variable according to each $F_s$. In the case of using an analog filter, for example, it is proposed that R and C in the apparatus are made to be variable and the cut-off frequency is controlled in accordance with the setting of CPU.

Problems caused in the above system are described as follows.

(1) Since this filter is realized in the analog circuit, the filter characteristic is changed in accordance with the environmental temperature and humidity. It is necessary to provide a complicated mechanism for the compensation of the change in the environmental temperature and humidity. Therefore, the reliability of the apparatus is deteriorated and further the cost of the apparatus is raised.

(2) Since the cut-off characteristic of an analog filter is very gentle, in order to make the amplitude at $F_g$ to be close to 0, it is necessary that the cut-off frequency ($F_c$) of the filter is set at a point considerably lower than $F_g$. FIGS. 10(a) to 10(c) are views showing the spectrum of an image signal obtained when an analog filter is used. When the analog filter shown in FIG. 10(b) is applied to the image shown in FIG. 10(a) in which the grid has been photographed, an amplitude of the image signal having no influence on moire artifacts is also suppressed. As a result, high frequency components of a digitalized image are reduced, so that the image sharpness is deteriorated as illustrated in FIG. 10(c).

There are two causes of moire stripes. One is aliasing of the spectrum described above, and the other is a phenomenon referred to as a beat. The phenomenon of a beat occurs when the following condition is satisfied.

$$F_g \approx F_s/2 \quad (3)$$

As illustrated in FIG. 11(a), the amplitude of a digitized image is different according to a case in which the image signal is sampled at a position close to the top of the amplitude of the grid image and also according to a case in which the image signal is sampled at a position close to the center of the amplitude of the grid image, and as illustrated in FIG. 11(b), the envelope appears as an image of the frequency considerably lower than that of the grid image. According to the image density of the background, the degree of the influence of this phenomenon upon a human's eyes is different. In general, in a density range in which the background density is 0.6 to 1.2, human eyes are able to recognize the beat phenomenon as a problem. It is impossible to completely solve this problem by performing the filtering expressed by the above expression (2). Further, in the case of an analog filter, because of the above problem (2), it is very difficult to find the optimum condition for removing the beat phenomenon.

When the rotational speed R of the polygonal mirror is R=2000 rpm, the focal distance f of the Fθ lens is fθ=380 mm and the pixel size ($P_{size}$) is variable in the range from 100 to 200 μm, the pixel clock $F_{pix}$ can be expressed by the following expression.

$$F_{pix} = \frac{\frac{R}{60} \times 4 \cdot \pi \cdot f}{P_{size}} \quad (4)$$

Accordingly, the pixel clock $F_{pix}$ is variable in the range from 1.6 to 0.8 MHz. In this connection, the units are as follows. $F_{pix}$ is [Hz], R is [rpm], f is [m], and $P_{size}$ is [m]. In this embodiment, the frequency that is 16 times as high as the frequency of the pixel clock is generated by PLL circuit in the clock generator (19), and the frequency is divided into 1/16 by the frequency divider, so that the pixel clock can be obtained. In order to make the pixel size variable, a large number of oscillators may be changed over. In the methods described above, the rotational speed of the polygonal mirror is constant, however, it is understood from the expression (4) that the pixel size can be changed even when the rotational speed of the polygonal mirror is variable. It is possible that both the pixel clock and the rotational speed of the polygonal mirror are made to be variable. Commonly, the pixel is square. Therefore, when the pixel size in the primary scanning direction is variable as described above, the medium conveyance speed in the subsidiary direction is changed at the same time, for example, by changing the pulse frequency of a pulse motor. In this way, the pixel size in the subsidiary scanning direction can be made to be variable.

The operation of cut-off of the stationary LPF (14) is fixed at 0.8 Mhz that is ½ of the maximum pixel clock (sample frequency) 1.6 MHz. In this case, if the pixel clock is used for A/D conversion as it is, in the case where the sampling is conducted at the minimum pixel clock 0.8 MHz, a turn is generated in the digitalized image data. As a result, there is a possibility that moire strips are caused on the image.

U.S. Pat. Nos. 5,006,708 and 5,028,784 disclose a means for solving the above problems. For example, U.S. Pat. No. 5,006,708 discloses the following means. There is provided a digital filter to cut frequency components higher than the Nyquist frequency ($F_s/2$) for the purpose of removing noises at least in one direction of the recording sheet. U.S. Pat. No. 5,028,784 discloses the following means. There is provided a digital filter to cut frequency components higher than the turn component and the Nyquist frequency for the purpose of removing the moire caused by the grid at least in one direction of crossing the grid image. However, according to the above proposals, after the image information has been temporarily taken into the memory means, it is subjected to filtering processing. Therefore, it is necessary to provide an apparatus for storing the image information. Accordingly, the processing time is greatly increased. For the above reasons, it is desired to provide an apparatus having a simple structure by which the processing time can be reduced while moire artifacts generated by the grid are removed.

SUMMARY OF THE INVENTION

It is an object of the present invention to solve the problems caused when an image on which a grid image is photographed is digitalized in various pixel sizes.

The above object can be accomplished by an image reading apparatus comprising:

- a primary scanning means for scanning an original image recorded on a medium in the form of an image or a latent image in the primary scanning direction using a light beam;
- a clock signal generating means for generating clock signals, the frequency of which is N times as high as the frequency of a sampling clock corresponding to a desired pixel size that has been set synchronously with synchronization signals from a scanning synchronization signal generation means, arranged close to the scanning position in the primary scanning direction, so that the means can provide image data, the amount of which is N times as much;
- a conversion means for converting a light beam generated from or transmitted through the medium into electric signals in the primary scanning operation and also for converting the electric signal into digital signals synchronously with the above clock;
- a sub-scanning means for conveying the medium simultaneously with the primary scanning in the sub-scanning direction at a speed that has been set in accordance with a desired pixel size;
- a filter means for applying a one-dimensional digital filter to the image data of N times over-sampled by the above conversion means with respect to the primary scanning direction; and
- a thinning means for thinning out the image data to 1/N after the filter means has been applied, wherein the filtering operation is conducted synchronously with the scanning synchronization signal generation means.

The present invention is to provide an image reading apparatus in which an image recorded on a recording medium in the form of a light and shade image or in the form of a latent image is scanned by a light beam. In the image reading apparatus, a photoelectrically converted analog signal is converted into a digital signal, and the thus obtained digital signal is applied to a digital filter. Further, several types of characteristics are provided for the digital filter, and the optimum characteristic is selected in accordance with the grid frequency and the sample frequency determined in the apparatus, and the thus determined characteristic is set in the filter. The apparatus of the present invention includes the aforementioned digital filter and the mechanism to set the optimum characteristic in the filter. Due to the above mechanisms, it is possible to read an image without the deterioration of image quality such as moire concerning various grid images.

BRIEF DESCRIPTION OF THE DRAWINGS

FIG. 8 is a graph showing the frequency characteristic when the number of taps is changed in the case of using a Hamming window and in the case of not using a Hamming window.

FIGS. 9(a) to 9(c) are schematic illustrations showing a mechanism of the generation of moire.

FIGS. 11(a) and 11(b) are schematic illustrations showing a beat phenomenon.

DETAILED DESCRIPTION OF THE INVENTION

With reference to the accompanying drawings, the present invention will be explained in detail.

The overall arrangement of the image reading apparatus is described below.

Figure 1:
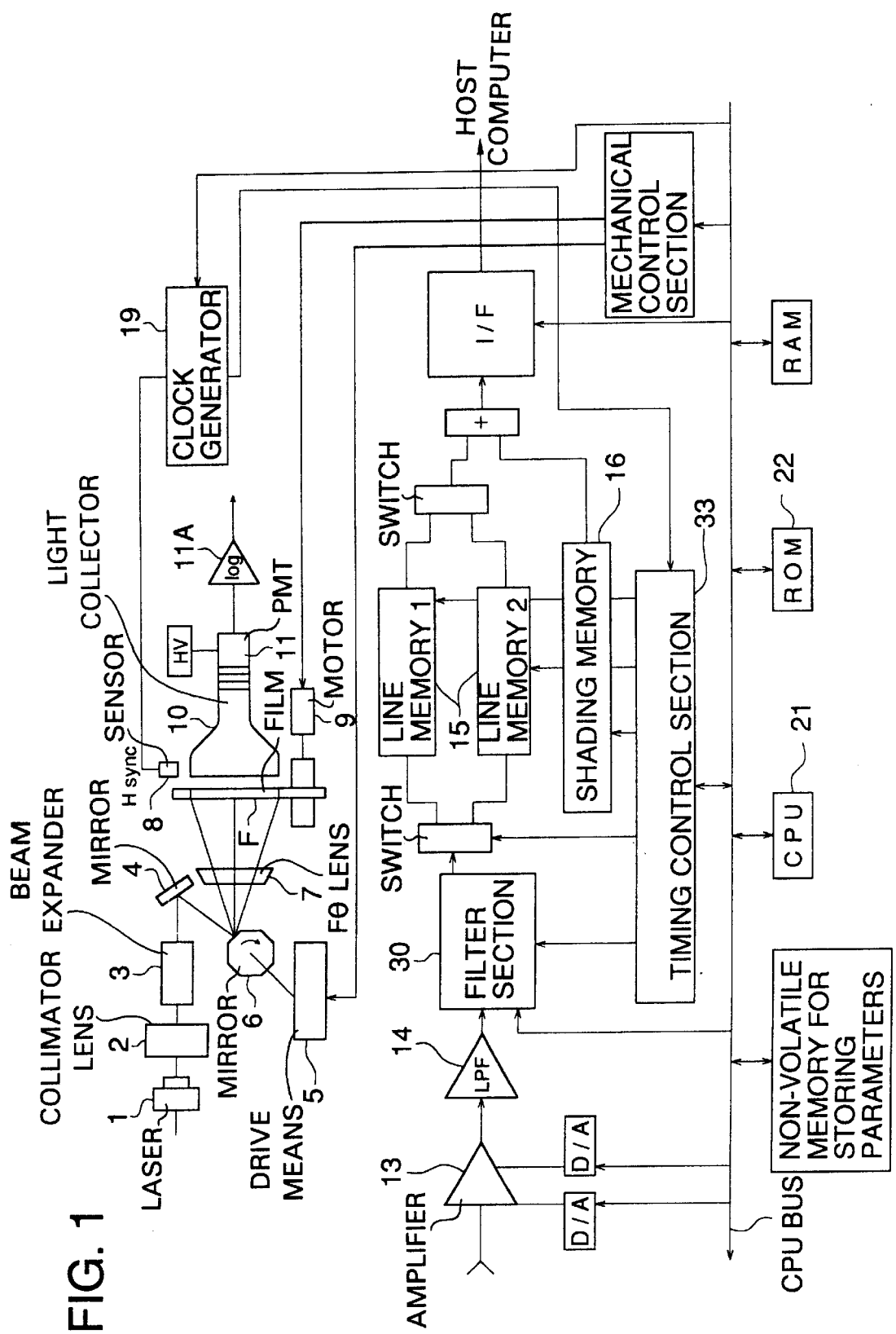
FIG. 1 is an overall arrangement view of the image reading apparatus of the present invention.

FIG. 1 is an overall arrangement view of the image reading apparatus of the present invention. A light beam to conduct scanning on an image medium such as an X-ray film for medical use is generated by the semiconductor laser (1). It can be considered to use He-Ne laser and Ar laser for the light source. However, in order to prevent the occurrence of the phenomenon of interference fringes on a digital image obtained when a portion of very low density is scanned by the image reading apparatus, it is preferable to use a semiconductor laser of the multi-spectra mode. In this embodiment, a semiconductor laser, the central frequency of which is 780 nm, is used, however, it possible to use any semiconductor laser, the central frequency of which is from 600 nm to 1000 nm. Further, a semiconductor laser, it possible to use a semiconductor laser, the central frequency of which is out of the aforementioned range. Of course, in this case, it is necessary to give consideration to the sensitivity of the photoelectric converter with respect to the wavelength. For example, in this embodiment, a photomultiplier, the sensitivity of which is high in the wavelength from 600 to 800 nm, is used. In this case, at the wavelength close to 600 nm, the sensitivity is high, which is preferable. Since a light beam, the wavelength of which is close to 600 nm, is visible to a human's eyes. Therefore, using a light beam, the wavelength of which is close to 600 nm, is very preferable.

A light beam emitted from the semiconductor laser (1) passes through a collimator lens (2), beam expander (3) and mirror (4). Then the light beam is incident on a polygonal mirror (6) rotated at a predetermined angular speed by a drive means (5). After that, the light beam passes through the Fθ lens (7) and forms an image on the film (F) which is an image medium. At a position close to the side of the film (F), that is, at a position on the scanning start side of the film (F), there is provided a sensor (H-sync sensor) (8) which is a primary scanning synchronization signal generating means used for synchronization with reading. Reading the image data is conducted in timed relation with a signal sent out from this sensor (8). There is provided a clock generator (19) for generating a clock, the frequency of which is N times as high as the sampling clock corresponding to a desired pixel size determined in synchronization with the signal of the sensor (8).

Primary scanning is conducted on the film (F) by a light beam reflected on the rotational polygonal mirror (6), and at the same time, the film (F) is moved in the sub-scanning direction by the motor (9) of the drive means at a speed determined by a desired pixel size. In this case, a pulse motor is used for the motor (9), however, it is possible to use a DC motor for the purpose of preventing the vibration caused in the rotation at low speed.

After the light beam has been transmitted through the film (F), it is converged by a light collector (10) composed of optical fiber. Then the light beam is sent into Photomultiplier tube (PMT) (11) used as a photoelectric converter and passes through a logarithmic multiplier (11A). After that, the gain and offset is adjusted by an amplifier (13) having a gain and offset adjustment function so that it can be matched to the characteristic of an A/D converter. Immediately before the A/D converter by which the analog value is converted into the digital value in synchronization with the clock, there is provided a low pass filter (LPF) (14) of the stationary cut-off frequency ($F_C$) for removing aliasing caused by sampling.

According to the present invention, the operation is conducted as follows. After that, the obtained signal is subjected to A/D conversion and the digital filter is applied. Then the signal gets into a line memory (15). There are provided two sets of line memories, and each line memory is used for the primary scanning. The line memories are changed over for each scanning operation. Further, there is provided a memory (16) for storing the shading correction data. In the memory (16) for storing the shading correction data, a value of the signal, that is, shading data, is stored, wherein the shading data is a signal value obtained when scanning is conducted under the condition that the film is not set in the apparatus. This data expresses a phenomenon of shading in which the signal value is changed according to the primary scanning position of the light beam in the optical system, the light converging system and PMT. When the A/D-converted data is stored in the line memory (15), the shading data is read out from the shading correction data storing memory (16) for each pixel, so that the data can be corrected. Theoretically, since the shading of the apparatus is linear, it is necessary that the image data and the shading data are subjected to multiplication or division. However, in this embodiment, the logarithmic amplifier (11A) is used for converting a signal of PMT (11) into a density value. Therefore, the shading correction can be performed by an addition. Accordingly, in this embodiment, the correction is conducted in such a manner that the shading data is deducted from the obtained image signal value for each corresponding pixel.

The structure of the signal processing section will be described below.

Figure 2:
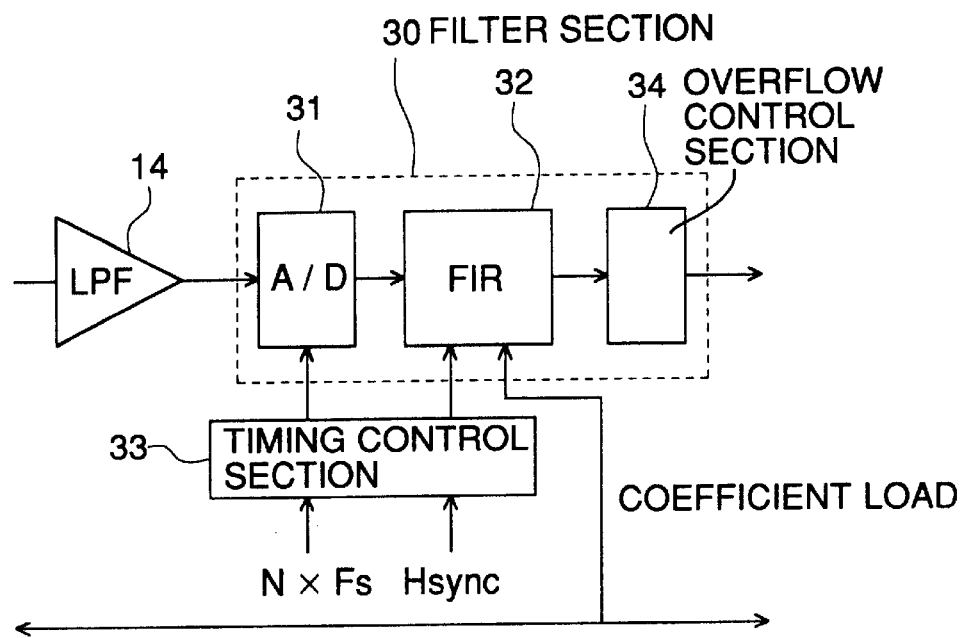
FIG. 2 is an arrangement view of the digital filter.

In this embodiment, in order to reduce the occurrence of moire and beat caused by a turn, the necessary operation is conducted in the analog filter (14) and the filter section (30) illustrated in FIG. 2. The operation will be explained in detail as follows.

The analog filter will be explained below.

In this embodiment, the rotational speed of the polygonal mirror is 2000 rpm, and the pixel size ($P_{size}$ in the expression (4)) is variable in the range from 80 μm to 200 μm. Therefore, according to the expression (4), the corresponding pixel clock frequency ($F_{pix}$) is variable in the range from 800 KHz to 200 KHz.

As described later, filtering is conducted in the present invention. Accordingly, in order to reduce an aliasing component contained in the image signal before filtering to a very small component so that problems do not arise in the filtering operation, A/D conversion is conducted by the frequency which is N times as high as the pixel clock frequency. Further, as described later, from the viewpoints of the number of bits of A/D-conversion and the signal-to-noise ratio, N is determined to be N=16 in this embodiment. Consequently, the maximum sample frequency is 12.8 to 32 MHz. Therefore, according to Nyquist's Sampling Theory, the cut-off frequency of the analog filter (14) immediately before A/D conversion must be not more than 6.4 MHz based on the sampling frequency. However, in the present invention, the frequency component of the final signal may be cut off at 1 MHz, which is the frequency at which a turn is not generated when the original pixel clock is made to be a sample frequency. Therefore, cut-off of the analog filter (14) may be conducted at any frequency from 1 MHz to 6.4 MHz. Accordingly, it is not necessary to use an analog filter of high accuracy. Therefore, the cost can be reduced. Concerning the characteristic of the analog filter, the important point is as follows. It is flat in the range from DC to 1 MHz. It is sufficiently attenuated when the frequency is not less than 6.4 MHz. Commonly, it is preferable to attenuate to be not more than 1/10 or 1/100.

The structure of the filter section will be explained as follows.

Figure 4:
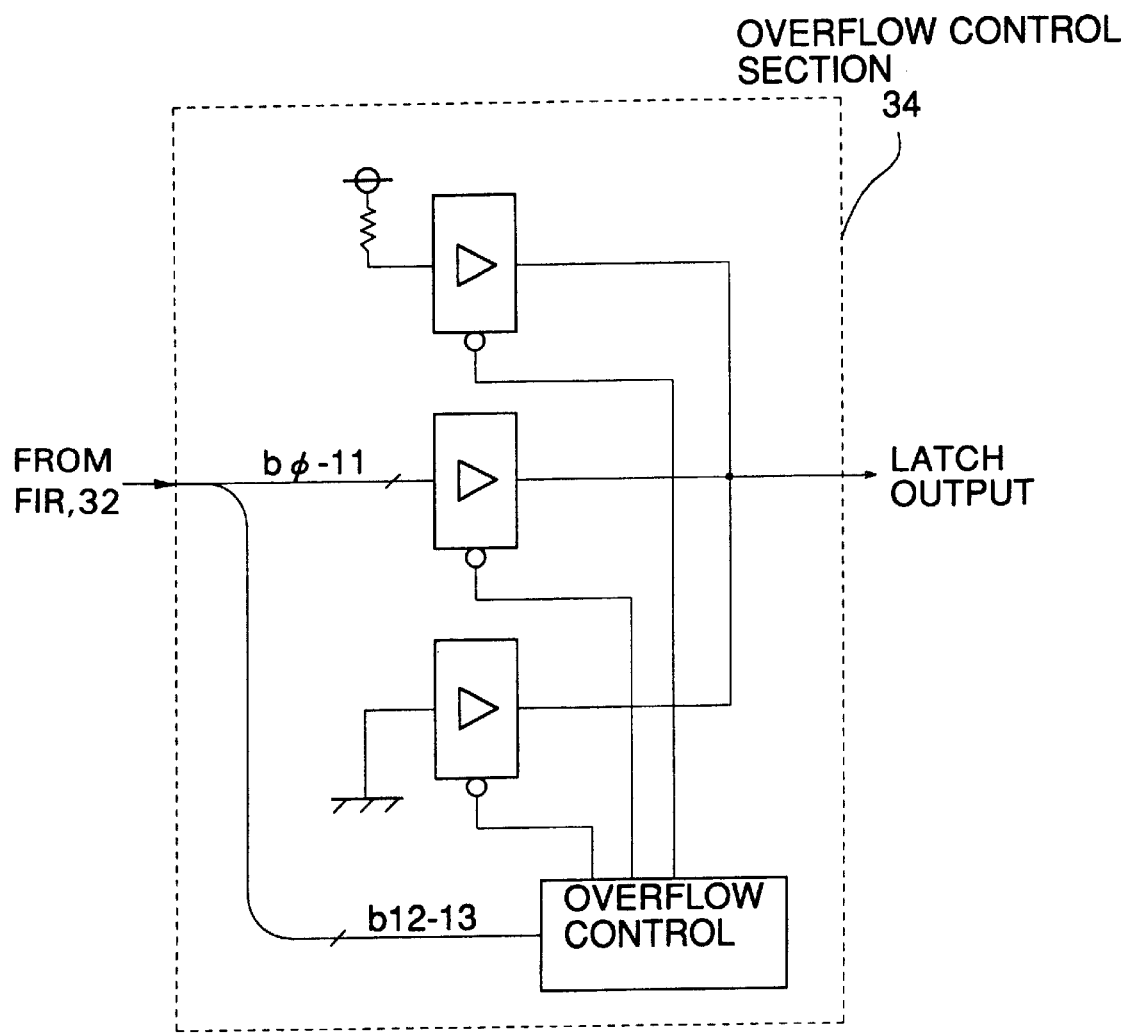
FIG. 4 is an arrangement view of the overflow control circuit.

As illustrated in FIG. 2, the digital filter section (30) includes: an A/D conversion section (31), a digital filter section (32) and a timing control section (33). Coefficients necessary for the operation of the digital filter are stored in the ROM installed in the filter or stored in the ROM (22) in which the program of the CPU (21) is stored, together with the program. The timing control section (33) has a function to generate the latch timing of the coefficients and the input and output data. Further, the timing control section (33) has a function to synchronize the primary scanning with the filter operation. It is possible for the CPU (21), which controls the reading apparatus, to make access to these sections. A signal of the digital filter section (32) is sent to the overflow control section (34), the detail of which is shown in FIG. 4.

The number of bits of the digital filter will be explained as follows.

In the case where the desirable image data is composed of 12 bits, the A/D converter 12, which is used without digital filtering, requires 12 bits. However, in this embodiment, the A/D converter uses 10 bits, and the sample frequency is 16 times as high as the pixel clock. The reason is described as follows.

According to "Analysis of the Digital Filter of which the Word Length Is Limited, and the Optimum Designing Method" on p. 112 of "Nikkei Electronics" published on Aug. 8th, 1977, the SN ratio of digitalized signals is expressed by the following expression.

$$SNR = 6 \cdot p + 10 \cdot \log\left(\frac{f_s}{W}\right) + 1.76 \qquad (5)$$

In the above expression, p is the number of bits of A/D conversion, $f_s$ is a sample frequency, and W is a frequency band.

As can be seen from the above expression, each time the number of bits is increased by 1 bit, the signal-to-noise ratio is increased by 6 dB, and each time the sample frequency is increased twice, the SN is increased by 3 dB. When the image data is composed of 12 bits, the signal-to-noise ratio is 72 dB. However, when the number p of bits is 10 and the sample frequency $f_s$ is increased by 16 times, the total SN is approximately 74 dB. Therefore, the signal-to-noise ratio is enhanced more than the original signal.

Consequently, when n bits are finally required as the image data, even if the number p of bits of A/D-conversion is p<n, the SN ratio can be maintained at the same level as that of the A/D converter of n bits when the sample frequency is multiplied by $2^{(n-p+1)}$ times.

When the digital filter processing is conducted as described above, it is possible to reduce the necessary bit accuracy so that the cost can be reduced.

Operation of the filter will be explained as follows.

Figure 3:
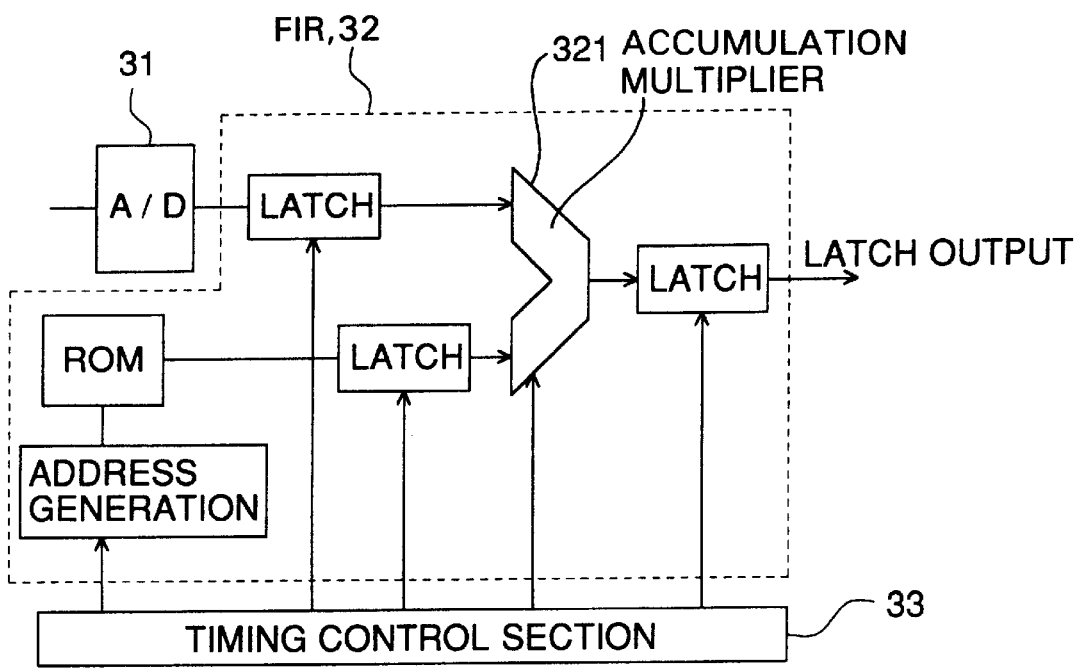
FIG. 3 is an arrangement view of the FIR filter circuit.

The digital filter of the embodiment is of FIR type illustrated in FIG. 3. This filter characteristic is realized in the following manner. A wave form obtained when the desired frequency characteristic is subjected to the Inverse Fourier Transformation is used as a coefficient. This coefficient is stored in the filter. When an A/D-converted input signal is subjected to the convolution operation using the coefficient, the filter characteristic can be realized.

When $D_{in}(n)$ is an input data row and $D_{out}(n)$ is an output data row, the operational expression of the FIR filter is expressed as follows.

$$D_{out}(n) = \sum_{k=-\frac{M}{2}}^{\frac{M}{2}-1} C(k) \cdot D_{in}(16n + k) \qquad (6)$$

In this case, M is the number of coefficients subjected to convolution, that is, M is the number of taps, and C(k) is k-th coefficient.

$$C(k) = \frac{S(k) \cdot W(k)}{\sum_{k} S(k) \cdot W(k)} \qquad (7)$$

In the above expression, S(k) is a Sync-function obtained when the rectangular window (ideal LPF) in the frequency region is subjected to the Inverse Fourier Transformation. S(k) is expressed by the expression (8). In the expression (8), D is a cut-off frequency based on the frequency of A/D-conversion. In the case of the expression (2), that is, when the cut-off characteristic of $F_s/2$ is obtained, since the A/D-conversion is conducted by $16F_s$ in the embodiment, the value of D is determined to be D $\frac{1}{32}$.

$$S(k) = \frac{\sin\left[2 \cdot \pi \cdot D \cdot \left(k - \frac{M-1}{2}\right)\right]}{2 \cdot \pi \cdot \left(k - \frac{M-1}{2}\right)} \qquad (8)$$

W(k) is a window function to reduce the separation from the ideal LPF characteristic caused when the number of taps is restricted. Examples of the window functions are: a rectangular window, a Hamming window, and a Blackman window. In this embodiment, the Hamming window is used. At this time, the function is expressed as follows.

$$W(k) = 0.54 - 0.46 \cdot \cos\left(\frac{2 \cdot \pi \cdot k}{M-1}\right) \qquad (9)$$

When the digital filter is used and one set of coefficients are prepared, it is possible to necessarily determine the cut-off frequency. Accordingly, it is not necessary to set the cut-off frequency with CPU each time, which is preferable. It is effective to prepare several coefficients by the expression (7) and reset the coefficient in accordance with the circumstances. In this case, it is required to conduct setting according to the command given by CPU. FIG. 8 is view showing the frequency characteristic when the number of taps is changed in two cases, wherein one is a case in which the window is not used and the other is a case in which the Hamming window is used.

Synchronization of the operation with the primary scanning will be explained as follows.

When the filter operation is actually conducted, the obtained data is finally thinned out to $\frac{1}{16}$. Therefore, it is necessary that the position of thinned data corresponds to the physical position of the medium. In the optical beam scanning apparatus used in the embodiment, a clock which is 8 to 16 times as high as the pixel clock is generated, and dividing is started at the rear end of the primary scanning synchronization signal (H-Sync signal). Due to the foregoing, a slippage of the physical position of the sampling conducted by A/D-conversion with respect to the position of the H-Sync sensor (8) can be always suppressed to be $\frac{1}{8}$ to $\frac{1}{16}$ of the pixel size. Accordingly, even when the image is expressed on CRT or printed by a printer, the image quality can be maintained at a high level. Specifically, the counter used for dividing is cleared by the H-Sync signal.

Since the pixel clock is 1.6 MHz at maximum in the embodiment, in order to conduct A/D-conversion at 16 times, it is necessary that the high frequency close to 26 MHz is synchronized with H-Sync. For this reason, it is necessary to provide a clock, the frequency of which is at least not less than 200 MHz that is 8 times. In order to realize the clock described above, it is required to use expensive logical elements, and further there is a high possibility of the generation of noise. Therefore, the cost is greatly raised to take countermeasures to prevent the generation of noise.

Figure 5:
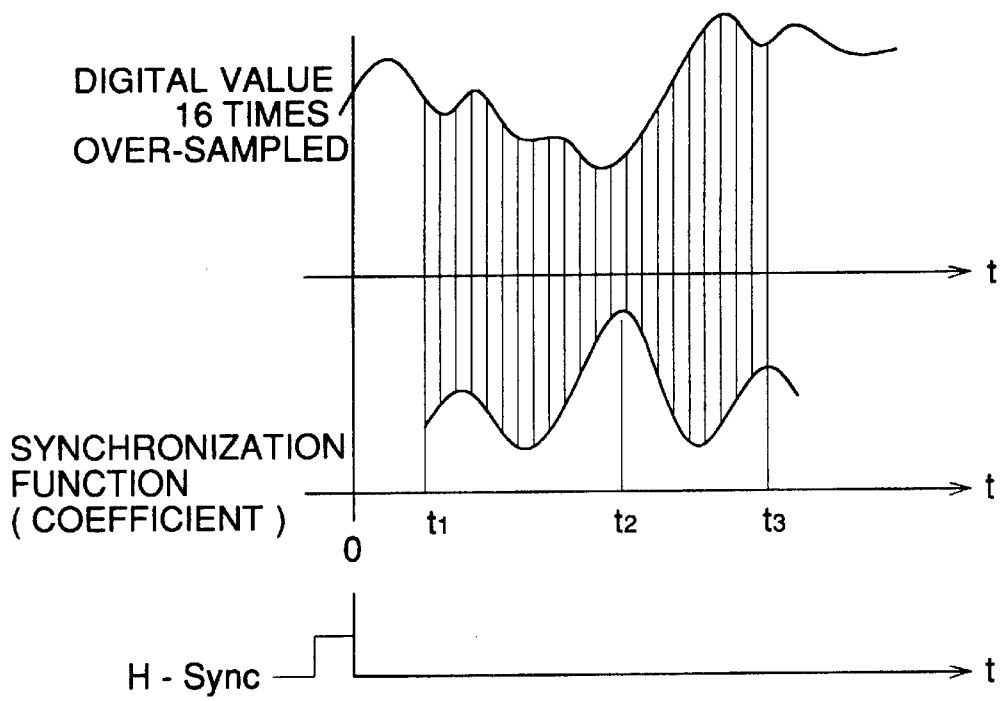
FIG. 5 is a schematic illustration for explaining a condition in which the output data of the digital filter is in synchronization with H-Sync.
Figure 6:
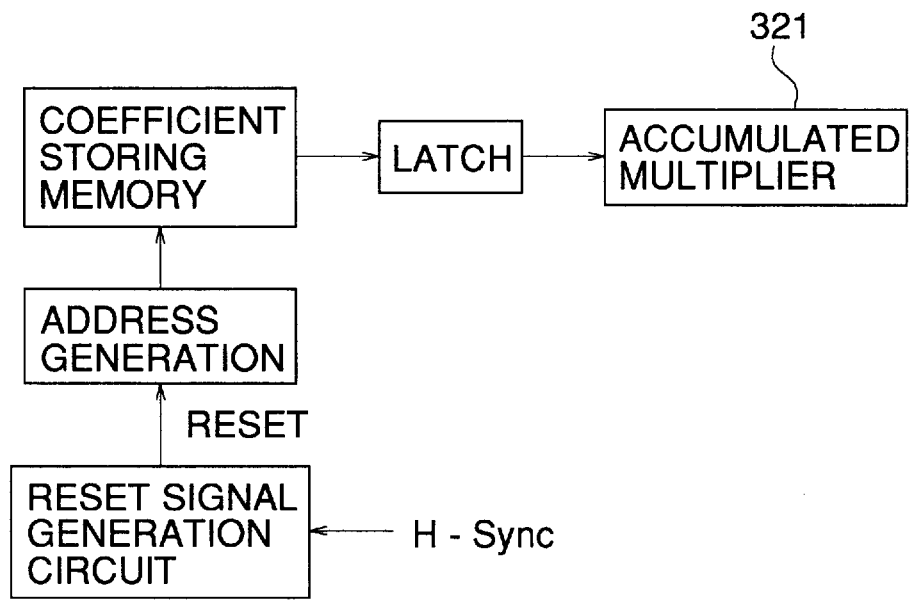
FIG. 6 is an arrangement view of the synchronization circuit with H-Sync in the digital filter operation.

Therefore, in this embodiment, as illustrated in the schematic illustration of FIG. 5 showing a condition in which the output data of the digital filter is synchronized with H-Sync, the A/D-conversion is conducted under the condition of non-synchronization, and only the operation is conducted in synchronization, so that the thinned output data of the digital filter can be synchronized with H-Sync. In other words, it is sufficient that the coefficient immediately after H-Sync surely starts at C(0). In order to realize this, the circuit is composed as follows. For example, as shown in the synchronization circuit of FIG. 6 in which the digital filter operation is synchronized with H-Sync, the address of ROM in which the coefficients are stored are reset by H-Sync.

The detailed structure of the digital filter section will be explained as follows.

The filter is composed in the structure of FIR (finite impulse response). As illustrated in FIG. 3, the digital filter section includes: a multiplier and adder, which conduct a latch at each 16th, wherein the accumulation multiplier (321) is commonly used; and a memory for storing the coefficients. However, in order to realize the FIR filter, it is necessary to conduct multiplications, the number of which is the same as the number of coefficients, that is, the number of taps. Consequently, the structure is determined by the speed of the multiplier to be used and the finally required image data speed. For example, consideration is given to a case in which writing is conducted on the line memory under the following conditions. The number of taps is 100, the speed of the multiplier is 100 ns, and data is written at 1 $\mu$s/pixel. When one multiplier is used, multiplication is conducted only 10 times. Therefore, at least 10 multipliers must be operated. It is possible to adopt the structure described above, however, in order to prevent the circuit from extending in its size, it is possible to realize the object by using an exclusive LSI such as L64245 manufactured by LSI Logic Co.

It is possible to consider another method in which a digital filter of IIR type is used. In this case, the method of making coefficients and the structure of a filter circuit are different from those of FIR. In general, in the case of IIR filter, there is provided a feedback loop in the circuit, and it is possible to realize an infinite impulse response by the coefficients of which the number is finite. Accordingly, IIR is advantageous in that a sharp filter characteristic can be realized by the coefficients, the number of which is smaller than that of the FIR filter structure. However, in this embodiment, FIR structure is used because the coefficients are relatively simply made.

The number of taps will be explained as follows.

When the desired frequency characteristic is rectangular, theoretically, the number of coefficients is infinite. However, the number of coefficients in the actual operation is finite because of the restriction of the circuit. The more the number of coefficients is, the more rectangular the filter characteristic becomes, and the cut-off characteristic becomes sharp in the area close to the cut-off frequency. Accordingly, the phenomenon of moire can be removed more effectively. In other words, attenuation can be avoided in the necessary frequency band lower than the cut-off frequency, and a high attenuation ratio can be provided in the frequency band higher than the cut-off frequency, so that the image sharpness is not deteriorated.

According to the result of the experiments made by the present inventors, the following was confirmed. In order to prevent the occurrence of the phenomenon of moire, it is necessary that the intensity of the grid image signal is attenuated to at least 1/25. When the above Sync-function is combined with the hamming window, it is possible to provide a ratio of attenuation of about 1/100 in the cut-off band frequency band.

In this case, 208 taps are used, however, 100 taps are available. However, when the number of taps is reduced small, for example, when the number of taps is reduced to 50 or 25, the substantial characteristic is greatly separate from the design value of the filter. Therefore, it is difficult to set the optimum cut-off, and further the attenuation is increased in the passage frequency band. Accordingly, in the same manner as the analog filter, there is a possibility that the frequency characteristic of the image is affected.

Prevention of overflow will be explained as follows.

In order to prevent the occurrence of overflow, the filter coefficients are normalized in the operation and stored in ROM. However, the bit length is finite. Therefore, a difference (quantization error) is caused between the normalized coefficient and the coefficient computed by the real numbers, which causes an overflow. When an overflow occurs in the operation, a density region not existing in the original image is generated. For example, when 000 of 12 bit data expresses a low density and FFF expresses a high density, as a result of the operation, the place of the figure is taken up. Accordingly, the data expected to be close to FFF becomes 000 with respect to the lower 12 bits. For this reason, a portion on the image, which is originally black, becomes white. When the data lower than 000 is generated, it is possible that the inverse phenomenon is caused, which is an underflow. In order to prevent the occurrence of the above phenomenon, when it is detected that the place of figure has been taken up, the value is forcibly fixed to the maximum or minimum value, that is, the value is forcibly fixed to 000 or FFF.

Therefore, the present embodiment is composed as follows. When the output of n bits is finally made as the image data, the data of at least m bits (m>=n +1) is made to be an output of the digital filter. In accordance with the bit pattern of the upper bit (m−n+1), the maximum value, the minimum value and the result of the operation of the digital filter are selected as the image data and outputted to the lower n bits of the digital data. That is, the accuracy of operation is increased by 1 bit more than the number of bits which is essentially required, and the upper bit is used for the detection. In the case of operation in which no signs are used, when the data of 13 bits can be taken out with the accuracy of 12 bits, it is 0 0000 0000 0000 to 0 1111 1111 1111.

In the case of an overflow/underflow, it becomes 1 1111 1111 1111 to 1 0000 0000 0000. When the uppermost 2 bits are 11, it is possible to detect an underflow, and when the uppermost 2 bits are 01, it is possible to detect an overflow. In the case of an underflow, 000 is outputted, and in the case of an overflow, FFF is outputted, and in the case of other bit patterns, the result of operation of the digital filter is outputted as it is. Due to the foregoing structure, it is possible to prevent the occurrence of abnormality on the outputted image. In this case, the circuit is shown in FIG. 4.

In the case of data in which the signs are used, the detection can be conducted by the upper 2 bits in the same manner.

(Normal) 1 1000 0000 0000 to 0 0111 1111 1111

(Abnormal) 1 0111 1111 1111 to 0 1000 0000 0000

In the above example, one more bit is used for the detection of an overflow/underflow, however, it is possible to use not less than 2 bits. When the foregoing is generally expanded, the following can be concluded. In order to detect an overflow or an underflow with respect to the necessary bit number n (in the above case, n=12), the bit number not less than m=n+1 (in the above case, m=13) is required. According to the pattern of the upper m−n+1 bits (in the above case, the upper 2 bits), the output value is selected from the maximum, the minimum and the result of operation. The aforementioned mechanism is required to solve the problems of an overflow/underflow.

Removal of the beat phenomenon, and the system structure will be explained as follows.

Figure 7:
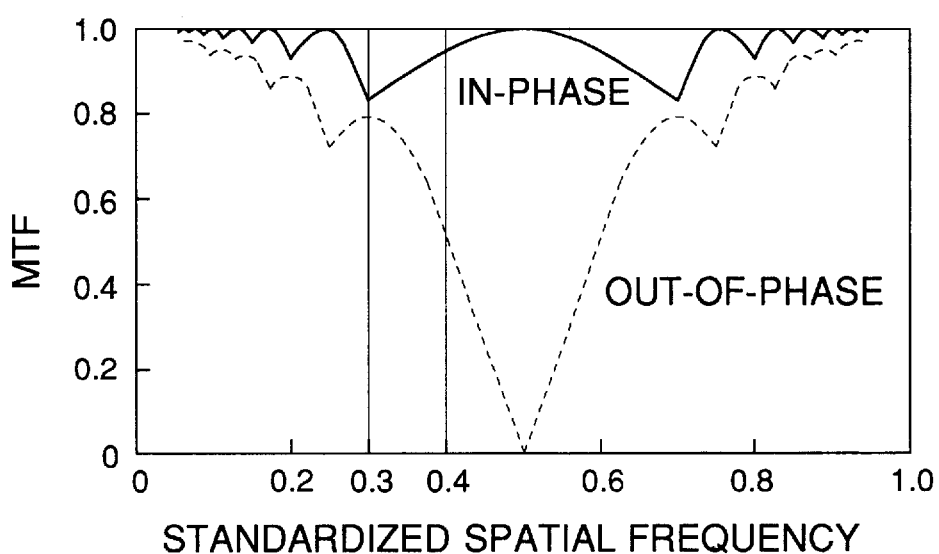
FIG. 7 is a graph showing a relation between the sample frequency and MTF with respect to IN-PHASE and OUT-OF-PHASE.
Figure 10:
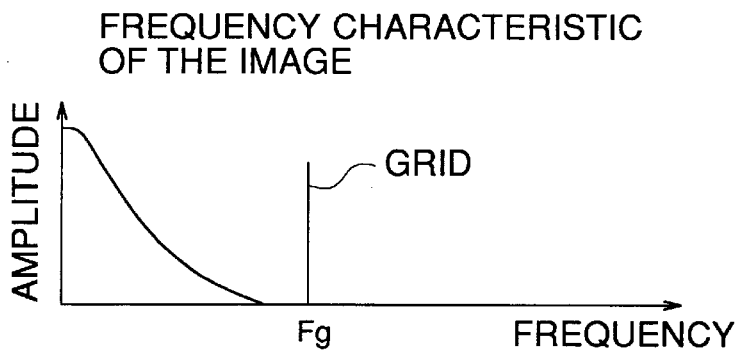
FIGS. 10(a) to 10(c) are image signal spectrums in the case of using an analog filter.
Figure 10:
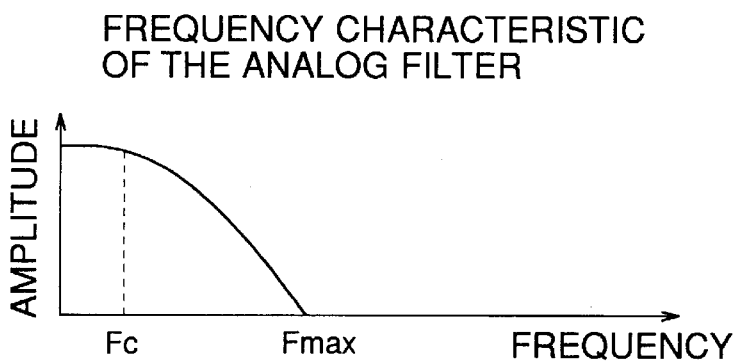
Figure 10:
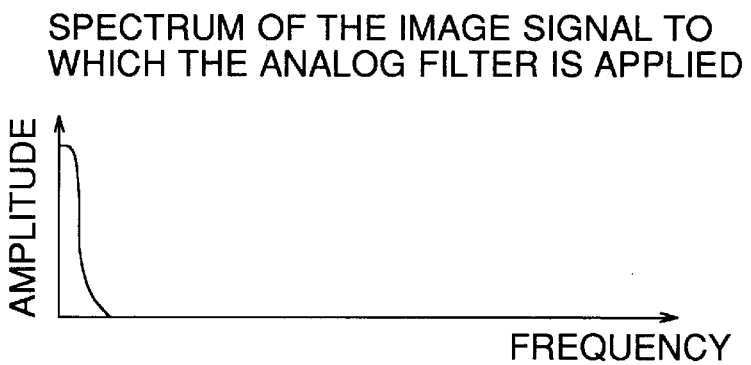

The beat phenomenon is discussed in the treatises of the Electronic Communication Society Vol. J59-C No. 7 p. 451 "Characteristic of Resolving Power in the Vertical Direction of the Frame Transfer Type CCD Image Pick-up Element". In order to reduce the amplitude, it is necessary to cut off the frequency component of the image signal at a lower frequency than the cut-off frequency stipulated by the expression (2). FIG. 7 is an excerpt of the above document. Due to the foregoing, the amplitude of the beat phenomenon is suddenly decreased at a point of about $F_s/3$ indicated by the present inventors. Consequently, when the cut-off frequency is set at a point close to $F_s/3$, the beat phenomenon can be effectively prevented. This frequency is referred to as a beat removal cut-off. According to the result of the experiments made by the present inventors, it is clear that the beat phenomenon can be substantially positively removed when the beat removal cut-off is decreased to $F_s/3$. Depending upon the density of the photographed grid image, the beat phenomenon can be removed even in the case of cut-off higher than $F_s/3$. In order to maintain the sharpness of an image, it is preferable that the cut-off is conducted at a frequency as high as possible. Accordingly, it is most effective that an operator sets the beat removal cut-off while he checks the image quality on a CRT or a printed sheet.

As can be seen from FIG. 7, the beat phenomenon is most remarkable when the grid frequency $F_g$ substantially coincides with ½ of the sample frequency $F_s$. When the spatial frequency is taken into consideration, the beat phenomenon is most remarkable when the double of the pixel size found by the expression (4) coincides with the period of the grid image. For example, when 60 pieces/mm of grids are used, the period is 167 μm, however, when the pixel size is 84 μm which is ½ of the period is 167 μm, the beat phenomenon becomes most remarkable.

When the pixel size is selected so as to satisfy the following expression, the beat phenomenon tends to occur most frequently.

[Pixel Size]=[Grid Period]/2    (10)

When the cut-off frequency of the filter is set, for example, at $F_s/3$, it is possible to prevent the occurrence of the beat phenomenon.

However, when an image is digitalized, the image sharpness can be enhanced by reading as high frequency components as possible. Therefore, the following is most effective. Usually, it is commonly set at $F_s/2$. Only when there is a possibility that the beat phenomenon occurs so that the image quality is deteriorated, it is shifted to the beat removal cut-off frequency.

Specifically, the cut-off frequency may be set through a key board connected to the reading apparatus or an operational switch mounted on the control base plate. The operator judges whether or not the condition satisfies the expression (2), from the grid density used for photographing and the pixel size used for reading, so that the operator can set the appropriate cut-off frequency.

As described in this embodiment, the image reading apparatus for medical use is commonly connected to the host computer. It is possible for the operator to operate the host computer in such a manner that the operator does not set the specific cut-off frequency but sets the grid density used for photographing. In this case, the cut-off frequency is set as follows. A table for finding the most appropriate cut-off frequency from the used pixel size is previously recorded in ROM. According to the table, the cut-off frequency of the digital filter is selected and set on the filter.

The following is an example of the table on which 3 sets of filter cut-off frequencies, which are $F_s/3$, $F_s/2$ and $2F_s/3$, are prepared. As can be seen from the example, when 3 sets of filter cut-off frequencies are used, the object can be accomplished without using the table.

The relation between the grid period $(G_{size})/2$ and the pixel size $(P_{size})$ is shown below.

| [Relation] | Cut-off Frequency to Be Used |
|---|---|
| $G_{size}/2 >= P_{size}$ | $F_s/2$ |
| $G_{size}/2 < P_{size}$ | $F_s/3$ |
| No grid | $2F_s/3$ |

In order to further automatize the above mechanism, it is possible to employ the following method. When an image is photographed with X-rays, the existence of a grid and the density of the grid are photographed together with the name of a patient, or when a bar-code label is recorded on the medium together with an image to be recorded, the data can be automatically recognized when the reading apparatus reads the recorded data, so that the cut-off frequency can be set with reference to the above table.

In the case of the above mechanism, the image data can be provided as follows. First, a filter having the cut-off frequency of $F_s/2$ at a predetermined pixel size is used and the data is digitalized. After that, the grid density information photographed on the image is read. When it is judged that a beat phenomenon tends to occur according to the pixel size, the cut-off frequency is automatically set at $F_s/3$, and the data is digitalized again using the same pixel size, and the thus obtained data is used as the final image data.

According to the above structure, concerning an X-ray photograph taken under the condition of no grid, it is possible to set the cut-off frequency at a value higher than $F_s/2$ so as to maintain the sharpness of the image. In the case of a normal X-ray image, even when the cut-off frequency is set approximately at $F_s \cdot 2/3$, image deterioration is not caused by a turn, but edge portions of characters and labels are effectively made to be clear.

As described above, it is very effective to compose the image reading apparatus in the following manner. The cut-off frequency of the filter is made to be variable in the range from $F_s/3$ to $2F_s/3$, and the data to be digitalized such as a grid density is maintained so that it can be selected. After the data has been once digitized, the cut-off frequency may be adjusted again when the operator monitors the digitized data on an image display means such as CRT. The cut-off frequency may be adjusted by visual inspection, and further the spatial frequency component of the image may be analyzed and the adjustment may be conducted in accordance with the result of the analysis. In order to minimize the influence of a aliasing, the variable range of the cut-off frequency may be set in the range from $F_s/3$ to $F_s/2$. When the variable range is set as described above, no problems are caused.

According to the present invention, the following image reading apparatus is provided. It is possible to solve problems caused when an image on which the grid image has been photographed is digitized by various pixel sizes, so that the image is not affected by the grid image. Further, without the deterioration of high frequency components on the digitized image, image sharpness can be maintained to be high.

What is claimed is:

1. An image reading apparatus, comprising:

a primary scanner for scanning an original image with light in a primary scanning direction, said original image being an X-ray image obtained using a grid and being recorded on a recording medium as one of an image and a latent image;

a clock signal generator for generating clock signals having a frequency N times as high as a frequency of pixel clock signals, wherein said pixel clock signals correspond to a desired pixel size, and wherein N is a positive integer;

a converter for converting a light beam from said recording medium into electric signals by a scanning operation of said primary scanner, and for converting said electric signals into digital signals based on said clock signals generated by said clock signal generator;

a low pass filter having at least one set of filter characteristics having a cut-off frequency between $\frac{1}{3}$ and $\frac{2}{3}$ of said frequency of said pixel clock signals for filtering said digital signals converted by said converter;

a thinning mechanism for thinning out said digital signals filtered by said low pass filter to 1/N in said primary scanning direction; and a memory for storing a plurality of said filtering characteristics of said low pass filter;

wherein said plurality of said filtering characteristics includes said cut-off frequency of $\frac{1}{3}$ of said frequency of said pixel clock signals; and wherein said low pass filter has a filtering characteristic which is selected in relation to a grid density of said grid and at least one of said desired pixel size and said frequency of said pixel clock signals.

2. The image reading apparatus of claim 1, wherein said low pass filter has a finite impulse response structure.

3. The image reading apparatus of claim 1, further comprising a flow controller for determining said digital image data in n bits obtained after said filtering operation of said low pass filter, said flow controller obtaining said digital image data from said low pass filter in m bits and determining said digital image data in n bits according to a bit pattern of upper bits, wherein m≧n+1, and wherein a number of said upper bits is m−n+1.

4. The image reading apparatus of claim 1, wherein said converter includes an A/D converter in p bits and said digital image data is in n bits, wherein p<n, and wherein said positive integer N>2 (n−p+1).

5. The image reading apparatus of claim 1, further comprising an input unit for inputting said grid density, wherein said input unit inputs said grid density by reading additional information which is recorded on said recording medium with said original image.

6. The image reading apparatus of claim 5, wherein said additional information includes at least one of a character and a bar code.

7. The image reading apparatus of claim 1, further comprising:

a scanning synchronization signal generator for generating synchronization signals for synchronizing said scanning operation of said primary scanner with an electric to digital signal conversion operation of said converter;

wherein said converter converts said light beam from said recording medium into said digital signals in synchronism with said clock signals generated by said clock signal generator.

8. The image reading apparatus of claim 1, further comprising:

a scanning synchronization signal generator for generating synchronization signals for synchronizing said scanning operation of said primary scanner with an electric to digital signal conversion operation of said converter;

wherein a filtering operation of said low pass filter is conducted synchronously with said synchronization signals generated by said scanning synchronization signal generator.

* * * * *